(12) United States Patent
Spartz et al.

(10) Patent No.: US 10,393,710 B2
(45) Date of Patent: Aug. 27, 2019

(54) COUPLED ANALYTICAL INSTRUMENTS FOR DUAL MODE FTIR/GC-FTIR

(71) Applicant: MAX Analytical Technologies, Inc., East Windsor, CT (US)

(72) Inventors: Martin L. Spartz, Ellington, CT (US); Anthony S. Bonanno, Ellington, CT (US); Peter P. Behnke, Vernon, CT (US)

(73) Assignee: MLS ACQ, INC., East Windsor, CT (US)

( * ) Notice: Subject to any disclaimer, the term of this patent is extended or adjusted under 35 U.S.C. 154(b) by 80 days.

(21) Appl. No.: 15/335,618

(22) Filed: Oct. 27, 2016

(65) Prior Publication Data

US 2017/0122920 A1    May 4, 2017

Related U.S. Application Data

(60) Provisional application No. 62/249,220, filed on Oct. 31, 2015.

(51) Int. Cl.
*G01N 30/02* (2006.01)
*G01N 30/06* (2006.01)
*G01N 30/08* (2006.01)
*G01N 30/20* (2006.01)
*G01N 30/30* (2006.01)
(Continued)

(52) U.S. Cl.
CPC ............. *G01N 30/74* (2013.01); *G01N 30/06* (2013.01); *G01N 30/20* (2013.01); *G01N 30/30* (2013.01); *G01N 30/38* (2013.01); *G01N 2030/025* (2013.01); *G01N 2030/085* (2013.01); *G01N 2030/201* (2013.01); *G01N 2030/202* (2013.01);
(Continued)

(58) Field of Classification Search
CPC ....... G01N 2030/025; G01N 2030/743; G01N 30/06; G01N 30/30; G01N 30/38; G01N 30/74; G01N 2030/202; G01N 2030/085; G01N 2030/8886; G01N 2030/201; G01N 30/20
See application file for complete search history.

(56) References Cited

U.S. PATENT DOCUMENTS 3,686,923 A    8/1972   Favre
5,922,106 A    7/1999   Mowry et al.
(Continued)

FOREIGN PATENT DOCUMENTS

DE    36 19 301 A1    12/1987
EP    2 574 920 A1    4/2013

OTHER PUBLICATIONS

Restek Corporation Product Sheet for Thermal Desoprtion Tubes. 2008. Accessed online on May 4, 2018. < http://m.restek.com/pdfs/EVFL1065.pdf>.*

(Continued)

*Primary Examiner* — Jonathan M Dunlap
(74) *Attorney, Agent, or Firm* — HoustonHogle LLP

(57) ABSTRACT

A system and method are disclosed for analyzing samples, which includes a spectrometry system for detecting components of a sample; a gas chromatography column for separating the components of a sample; a first sample unit for receiving a first sample from a sample source; and a second sample unit for receiving a second sample from a sample source. Each sample loop unit allows independent processing of samples in preparation for analysis.

5 Claims, 11 Drawing Sheets

(51) Int. Cl.
  *G01N 30/38*  (2006.01)
  *G01N 30/74*  (2006.01)
  *G01N 30/88*  (2006.01)

(52) U.S. Cl.
  CPC .................. *G01N 2030/743* (2013.01); *G01N 2030/8886* (2013.01)

(56) References Cited

U.S. PATENT DOCUMENTS

| | | | |
|---|---|---|---|
| 6,000,274 A | 12/1999 | Lai et al. | |
| 6,112,602 A | 9/2000 | Mitra | |
| 9,766,219 B2* | 9/2017 | Wapelhorst | G01N 33/0011 |
| 2004/0178133 A1* | 9/2004 | Deguchi | G01N 30/20 |
| | | | 210/198.2 |
| 2011/0247403 A1* | 10/2011 | Liu | G01N 30/463 |
| | | | 73/61.55 |
| 2013/0134095 A1* | 5/2013 | Anderer | B01D 15/1878 |
| | | | 210/656 |
| 2014/0248708 A1* | 9/2014 | Coleman | G01N 33/0011 |
| | | | 436/141 |
| 2015/0260695 A1 | 9/2015 | Spartz et al. | |

OTHER PUBLICATIONS

Francis W. Karasek, Francis I. Onuska, Frank J. Yang, and Ray E. Clement, "Gas chromatography". Analytical Chemistry. 1984. 56 (5), 174-199.*

International Search Report and the Written Opinion of the International Searching Authority, dated Mar. 22, 2017, from International Application No. PCT/US2016/059002, filed on Oct. 27, 2016. Twenty pages.

Partial International Search, dated Feb. 1, 2017, from International Application No. PCT/US2016/059002, filed on Oct. 27, 2016. Four pages.

International Preliminary Report on Patentability, dated May 11, 2018, from International Application No. PCT/US2016/059002, filed on Oct. 27, 2016. 11 pages.

* cited by examiner

COUPLED ANALYTICAL INSTRUMENTS FOR DUAL MODE FTIR/GC-FTIR

RELATED APPLICATIONS

This application claims the benefit under 35 USC 119(e) of U.S. Provisional Application No. 62/249,220, filed on Oct. 31, 2015, which is incorporated herein by reference in its entirety.

BACKGROUND OF THE INVENTION

Spectrometry-based gas analyzers, such as Fourier transform infrared spectrometry (FTIR) gas analyzers, are becoming common for environmental compliance applications and process gas monitoring, in addition to other gas analysis applications. They are generally good for measuring compounds from 0.1 parts per million (ppm) to a few percent levels in an environmental exhaust, for example. On the other hand, spectrometry-based gas analyzers generally perform poorly when parts per billion (ppb) detection levels are required. Moreover, if too many compounds are present (e.g., greater than 10-20) or too many unknowns are present, the analysis of the spectral data becomes too difficult and the results somewhat questionable.

Gas chromatography (GC) is an analytical method that measures the content of various components in a sample. The method for separating chemical substances relies on differences in partitioning behavior between a flowing mobile phase (gas phase) and a stationary phase supported in a column to separate the components in a mixture. As the gas flow passes through the column, the components of the sample move at velocities that are influenced by the degree of interaction of each component with the stationary phase in the column. Consequently, the different components separate as the components elute from the column.

Gas chromatography can be utilized for many compounds but also has many drawbacks, which include a need for full peak separation to qualify and quantify compounds present, small sample sizes and dynamic ranges, and continuing calibration.

Combined GC-FTIR systems are also known in the industry but are not widely accepted because other GC detectors are more sensitive.

SUMMARY OF THE INVENTION

The present invention selectively couples at least one of: a gas source and a calibration source to a spectrometric system, or to a chromatographic system and spectrometric system. Such an arrangement allows for many semi-volatile organic compounds (SVOCs) and volatile organic compounds (VOCs), for example, to be possibly separated and then analyzed.

One objective is to allow source testers or project/process engineers who utilize FUR gas analyzers to measure more compounds in an environmental or process gas stream than can currently be done today. The invention can allow compounds that cannot be measured directly by spectrometric analyzers, e.g., FUR gas analyzers, to be collected, possibly concentrated, separated and analyzed and then measured by the same spectrometric analyzers.

In this case, to have an optimal and/or complete test a one that tests compliance with certain requirements or protocols or Environmental Protection Agency EPA rules), one needs an analyzer that can measure the sample, e.g., environmental, stream and analyze it for as many compounds as possible, especially those that are too high in concentration to be handled by GC, cannot be concentrated enough for FTIR detection or otherwise not readily amenable for chromatography.

In one configuration, while compounds in one sample are being analyzed in real-time or near-real-time, a second sample is being collected, possibly concentrated and otherwise being prepared for separation and analysis. Once the real-time analysis of the first sample is finished, the second sample can be directed to the separation system, which separates the components of the sample in time, and then passes the components on to the spectrometric system for analysis.

An advantage over prior methods includes allowing for a more complete analysis of the sample to be performed. Gases that are too high in concentration for GC separation, cannot be trapped, or cannot be concentrated, can still be measured directly by the spectrometry system. Components that are too dilute and/or heavily mixed to be measured directly by the spectrometry system are instead first possibly concentrated and possibly separated by a chromatographic system and then subsequently analyzed by the spectrometry system.

The approach can allow for potentially hundreds of SVOCs and VOCs to be distinguished within a sample. Further it may allow for the SVOCs and VOCs to be measured at much lower levels than has been possible in the past.

The approach can be used for source testing, process monitoring, continuous emission monitoring (CEM), hazardous air pollutants (HAP) testing, break through studies, and inorganic and/or organic measurements for numerous potential compounds.

In one example, instruments constructed according to the principles of the present invention can be configured and reconfigured between a number of different modes of operation, including: 1. direct from sample source to the spectrometric system, 2. concentrate in a concentration device such as on thermal desorption tubes (TDT) or in a cryotrap, then direct to spectrometric system, and 3. optionally concentrate in the concentration device, then through GC and then to the spectrometric system.

In general, according to one aspect, the invention features an analysis system that is configurable for a spectrometric mode in which it performs spectrometric analysis on samples and a separation and spectrometric mode in which it first separates the samples into one or more respective components and then performs spectrometric analysis on the components of the samples.

Preferably, the analysis system has a chromatographic system for separating the samples into the components and possibly at least one concentrator for concentrating components from the samples prior to separation.

In general, according to another aspect, the invention features an analysis system that performs spectrometric analysis on samples simultaneously with concentrating samples for subsequent spectrometric analysis.

In general, according to another aspect, the invention features an analysis system that performs spectrometric analysis on samples taken upstream of an abatement system while capturing samples downstream of the abatement system.

In general, according to another aspect, the invention features an analysis system for analyzing samples from a sample source. The system comprises a spectrometry system for detecting one or more components of the samples, a gas chromatography system for separating the samples into the components, a concentrator for concentrating the samples. The system is configurable for directing the samples: from the sample source to said spectrometry system; and/or from the sample source to the concentrator and directing concentrated samples to the gas chromatography system for separating the sample into the components and directing the separated components to the spectrometry system.

In examples, the concentrator is a thermal desorption tube and/or cold trap and the spectrometry system is a Fourier transform infrared spectrometry system.

In general, according to another aspect, the invention features an analysis system configurable between a first analysis mode and a second analysis mode. The analysis system comprises a spectrometric system for performing spectral analysis and a separator for separating a sample into components, in which, for the first analysis mode, the analysis system is configured for directing a sample to the spectrometric system for spectral analysis, without passing the sample through the separator and for the second analysis mode, the analysis system is configured for directing the sample to the separator prior to directing the sample to the spectrometric system for spectral analysis.

In one example, the system comprises a first sample loop unit and a second sample loop unit; wherein the first and second sample loop units are configured for performing one or more processes concurrently and independently.

In implementations, a first sample concentrator is provided in the first sample loop unit and a second sample concentrator is provided in the second sample loop unit. The first and the second sample loop units are configured for directing respective portions of the sample to the first and second sample concentrators prior to the portions of the sample being directed to the spectrometric system.

Typically, each of the first and second sample concentrator or is one of: a thermal desorption tube and/or a cryogenic trap.

In general, according to another aspect, the invention features an analysis method for an analysis system. The method comprises performing spectrometric analysis on samples and first separating the samples into their one or more respective components and then performs spectrometric analysis on the components of the samples.

In general, according to another aspect, the invention features an analysis system. The system comprises a separator for separating samples into components, a spectrometric system for performing spectral analysis on the components, and a first sample loop unit and second sample loop unit enabling simultaneous processing of the samples, such one sample unit can be collecting samples while the other is providing the collected samples to the separator.

An input director can be used for directing either source gas or carrier gas to the first sample loop unit and/or the second sample loop unit. Also, a mass flow control valve can be used for supplying carrier gas to the concentrating devices.

In general, according to another aspect, the invention features an analysis method. The method comprises alternately collecting samples in a first sample loop unit or second sample loop, after samples have been collected in either of the first sample loop unit or second sample loop, separating the collected samples into components and performing spectral analysis on the components.

The above and other features of the invention including various details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. As used herein, the term "and/or" includes any and all combinations of one or more of the associated listed items.

It will be understood that although the terms "first" and "second" are used herein to describe various elements, these elements should not be limited by these terms. These terms are used only to distinguish one element from another element. Thus, an element discussed below could be termed a second element, and similarly, a second element may be termed a first element without departing from the teachings of the present invention.

As used herein, the singular forms and the articles "a", "an," and "the" are intended to include the plural forms as well, unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present.

Figure 1:
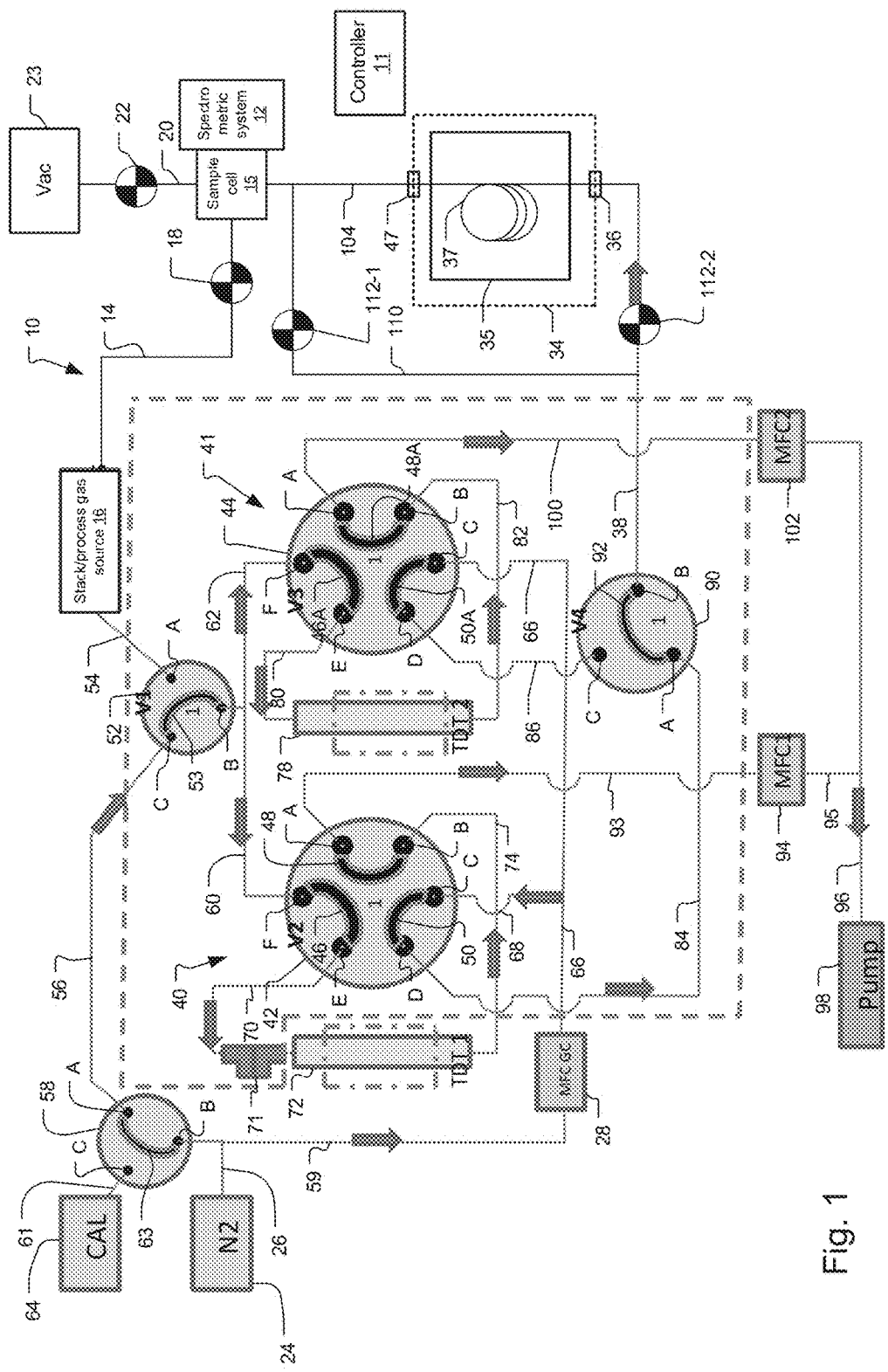
FIG. 1 is a schematic diagram of a dual loop sample analysis system for sampling and measuring hazardous air pollutants or other gas samples, according to embodiments of the invention, in dry mode.

An exemplary analysis system 10, which has been constructed according to the principles of the present invention, is shown in schematic form in FIG. 1.

The system 10 includes a spectrometric system 12 for detecting components, e.g., elements and compounds, of a sample stream. In different implementations, the spectrometric system determines the spectral response of the components in a sample cell 15 in one or more of the following spectral regions millimeter, microwave, terahertz, infrared (including near-, mid- and/or far-infrared), visible, ultraviolet (UV) (including vacuum ultraviolet (VUV)), x-rays and/or gamma. Further, the spectrometric system can measure different characteristics, such as absorption spectra, emission (including blackbody or fluorescence) spectra, elastic scattering and reflection spectra, impedance (e.g., index of refraction) spectra, and/or inelastic scattering (e.g., Raman and Compton scattering) spectra of the components in the sample cell.

In the case of optical spectrometric systems, for example, different technologies can be employed. In FTIR systems, single beam spectra are generated by taking the raw interferograms from the FUR spectrometer and then converting those interferograms to intensity versus wavenumber spectra. Then, sample and background single beam spectra are used to create the absorbance spectra.

In other situations, spectra might be directly read-out as in the case where the spectrometric system 12 is a post dispersive system, which includes a broadband source and a spectrally resolving detector system. In other examples, the spectrometric system 12 includes a tunable optical source (e.g., tunable laser) and a detector. Here, the spectral information is a function of the time response of the detector, in such a pre-dispersive, spectrometry system.

In general, the spectrometry system 12 is preferably sufficiently sensitive to detect at least some of the sample components with low concentration, such as at least in a few percent to low parts per million concentrations. Identified components of the sample and their concentrations are detected and analyzed by the spectrometry system. These data are compared with known predetermined concentrations that the spectrometry system is capable of sufficiently detecting.

Nevertheless, often other components are not sufficiently concentrated to be adequately identified and measured. As a result, in the same analysis system 10, a sample can be first concentrated prior to detection and analysis in the spectrometric system 12. In these circumstances, the samples are passed through a concentrator and/or separation system and then analyzed in the spectrometric system 12. Examples of concentrators suitable for such purpose are thermal desorption tubes (TDT) or cold (cryo) traps. Further, if the samples have trace concentrations, for example in the parts per billion or parts per trillion, a series of concentrators can be used in the analysis system 10. Such configurations allow the same system to be used for a wide variety of samples and sampling conditions.

In one embodiment, the spectrometric system 12 is a FTIR spectrometry system. The spectrometric system 12 has an inlet for receiving a sample stream line 14 from sample source 16 into its sample cell 15. The sample can be taken from a number of sources including exhaust gases (stack gases) having mandated environmental testing and process gas monitoring. Line 14 has a valve 18 for controlling and shutting off flow to the spectrometric system 12. The sample cell 15 of the spectrometric system 12 has an outlet for venting the sample contents from its sample cell 15 therein through line 20. Exit line 20 has an exit valve 22 for sealing and controlling flow from the sample cell 15 of the spectrometry system 12.

The analysis system 10 includes a controller 11. The spectrometry system 12 is in communication with the controller 11 that also functions as a data analyzer and data recorder and logger. The controller is a computer, which is programmed to collect the spectral data from the spectrometry system 12, process the spectral data, analyze the data and record and report the compounds present with their concentrations or mass to an operator via a user interface or to another computer. These data are compared with known preset amounts of concentrations (e.g., determined in a calibration procedure) that the spectrometry system 12 is capable of detecting.

The controller 11 is also programmed to control the flow of gases and liquids throughout the system 10 by controlling the valves, mass flow control valve, concentrators, separators, pumps, and directors in the system 10. The electrical control connections are not shown.

In a typical mode of operation, the sample flows through the gas cell 15 and out through the exit valve 22 and multiple spectra are obtained over time by the spectrometry system 12 and possibly averaged for detection limit reduction, i.e., enhancing detection sensitivity. In this mode, valve 22 is held open and a vacuum pump 23 operated to draw the gas through the sample cell 15.

In another, integrating, mode of operation, the gas cell 15 is used to collect a sample for a certain time period before performing spectral analysis on the sample. Here, the sample cell 15 has been partially or fully evacuated by the controller 11 opening valve 22 and operating the vacuum pump 23. Then, the valve 22 is closed and the vacuum pump 23 turned-off by the controller 11. Successive components from a sample are then allowed to accumulate in the sample cell 15, effectively integrating their spectral signatures. Multiple spectra obtained over a time interval can then be averaged to best measure the integrated concentration in the sample cell by the controller 11. Then, the final spectra are then used as a background spectra and new spectra are obtained, by the controller 11, as new components flow into the integrating sample cell. The spectra of the new components are obtained by comparing the current spectra to the background spectra. Then this process is repeated. Such a system is generally described in U.S. patent application Ser. No. 14/660,574, filed on Mar. 17, 2015, by Spartz, et. al., the teaching of this application being incorporated herein by this reference.

In embodiments, the sample cell 15 is a multiple pass cell such as a White cell or modified White cell with aspherical optics.

The analysis system 10 further includes a separator such as a gas chromatography (GC) system 34 that has a gas chromatographic column 37 for separating the different components from the sample in time. Often the column 37 is coiled in order to minimize the size while maintaining sufficient tube or column length. The GC column can also be used as a concentrating device but typically it is used for separation. For example, a sample could potentially be collected and concentrated on-column and then separated by the same column. An example of such compounds includes heavy compounds that are not very volatile such as pesticides and herbicides.

Column 37 has a proximate end or inlet 36 for receiving sample from sample inlet line 38 and distal end or outlet 47 for directing resulting product through line 104 to the spectrometry system 12. The system is configured to allow a concentrated sample to bypass the GC 34 to go directly from sample inlet line 38 to line 104 to the spectrometry system 12 if GC is not needed for a particular sample. The bypass line 110 includes a valve or valve system 112-1, 112-2 that when opened by the controller 11 allows for the bypass of the GC 34. Specifically, to bypass the GC, the bypass line valve 112-1 is opened and the GC line valve 112-2 is closed. On the other hand, when it is required to separate the concentrated sample into its components, is the bypass line valve 112-1 is closed and the GC line valve 112-2 is opened so that the concentrated sample flows into the GC 34.

The column 37 of the gas chromatography system 34 can be contained within a temperature controlled chamber 35 with a heat source (oven), such as a heating coil that is thermostatically controlled such as by the controller 11 in order to maintain a selected constant temperature during a gas chromatography analysis run. The heat source should also provide sufficient heat to the chamber interior so that a temperature is sufficiently high to ensure that the sample reaches a gaseous state. In GC columns, many compounds condense at the lower temperatures and slowly vaporize as the temperature goes up. Note that the inlet and injection port 36 can be heated separately from the chamber 35 so that it can be at much higher temperatures than the GC chamber 35 initially to ensure the sample is fully vaporized. The sample then condenses back onto the column, which starts initially at a cooler temperature, for example 35° C.

System 10 further includes first sample loop unit 40 and second sample loop unit 41. The two sample loop units allow independent and potentially simultaneous processing of samples, such as sampling, desorption, idling and drying. For example, one sample unit can be conducting sampling such as collecting and concentrating a sample, while the other is in a desorption mode in which a previously collected and concentrated sample is desorbed and conducted to the GC 34. Then the operation of the units 40, 41 can flip.

Each sample loop unit includes a sample director and thermal desorption tube (TDT) or a device for concentrating gas such as by thermal desorption or cryo focusing. The cryo trap requires a cryogen, such as liquid nitrogen.

In one embodiment, first sample loop unit 40 has first sample director 42 and second sample loop unit 41 has second sample director 44. First sample director 42 can operate independently of second sample director 44. This allows one director to direct a sample to the GC column for separation and FTIR for analysis the other director can capture and prepare the next sample for analysis. These directors 42, 44 can be manually operated and switched between different positions or they can be motorized using servos, for example, and controlled and operated by the controller 11 under automatic or preprogrammed control.

In more detail, first sample loop unit 40 has first sample director 42 which includes first tube loop 48, second tube loop 46, and third tube loop 50. First sample director 42 has a configuration that allows the tube loops to connect to different stationary ports A, B, C, E, and F in order to direct gases and/or liquids in a number of desired directions. In one embodiment, the first sample director is rotatable to allow tube loops to align with different ports A, B, C, E, and F in order to change direction of flow by forming a passage bridging the ports. As shown in FIG. 1, samples or carrier gases exiting TDT-1 can be returned to first sample director 42 through line 74, and samples or carrier gases exiting TDT-2 can be returned to the second sample director 44 through line 82 for further processing downstream.

Similarly, second sample loop unit 41 has second sample director 44 which is configured in the same manner as the first sample director. Second sample director 44 has first tube loop 46A, second tube loop 48A, and third tube loop 50A. Second sample director 44 has a configuration that allows the tube loops to connect to different ports A, B, C, D, E, and F in order to direct gases and/or liquids in a number of desired directions. In one embodiment the second sample director 44 is rotatable to allow tube loops to align with different ports A, B, C, D, E, and F in order to change direction of flow by forming a passage bridging the ports.

A first input director 52 is connected to line 54 for receiving source gas from source 16. As shown in FIG. 1, first input director 52 has tube loop 53 between points B and C to allow flow between those two points or ports, and port A is closed to prevent flow through first input director 52. First input director 52 has a configuration that allows the tube loop 53 to form a connection between two of the three ports A, B and C in order to direct gases and/or liquids in a number of desired directions. In one embodiment the first input director 52 is rotatable to allow its tube loop to align with different ports in order to change direction of flow. The rotation can be manually controller or controlled automatically by the controller 11.

Second input director 58 is connected to line 59 for receiving a second gas from a second gas source 24 through line 26 to line 59 to port B of the second input director 58 and directing it to the first input director 52. A second gas source 24 can be a carrier gas, such as nitrogen, helium or other essentially inert gas that will not interfere with detecting pollutants and other impurities. The second input director 58 is also connected through line 61 to a calibration gas source 64 for supplying a calibration gas for comparing the sample with a known composition. Second input director 58 is connected through line 56 for directing second gas or calibration gas to first input director 52 as desired.

As shown in FIG. 1 (i.e., daring a dry mode), second input director 58 has tube loop 63 between points A and B to allow flow between those two points, and point C is closed to prevent calibration gas flow through second input director 58. Second input director 58 has a configuration that allows by rotation the tube loop 63 to connect to different ports and corresponding gas lines in order to direct gases and/or liquids in a number of desired directions.

Line 59 also extends from second input director 58 and line 26. It is used to supply inert gas to mass flow control (MFC) valve 28. MFC valves are used to measure and control the flow of liquids and gases through the system. A MK valve can pulse the gas components from the GC column 37 into gas cell 15 by opening for a few seconds then the sample is analyzed for 30 seconds. The MFC valve is reopened. This allows one to have a much smaller set of data to analyze and fewer changes in concentration.

The output from MFC valve 28 is provided through line 66, which terminates at port C of the second sample director 44. Line 68 splits from line 66 and terminates at port C of the first sample director 42.

First sample director 42 is connected to first thermal desorption tube 72 (TDT-1) through port E which connects to line 70. Also on this line is a liquid sample injection port 71, which can be used for the injection of a liquid sample. TDT-1 can concentrate samples prior to detection and analysis in the spectrometry system 12. Samples are returned to first sample director 42 through line 74, which terminates at port B for further processing downstream.

Similarly, second sample director 44 is connected to second thermal desorption tube 78 (TDT-2) through port E, which connects to line 80. TDT-2 can concentrate samples prior to detection and analysis in the spectrometry system 12. Samples are returned to second sample director 44 through line 82, which terminates at port 13, for further processing downstream.

Sample exit director 90 is connected to line 84 through its port A for receiving gas/liquid from first sample director 42. Sample exit director 90 can also be connected to line 86 through its port C for receiving gas/liquid from the second sample director 44. Sample exit director 90 has tube loop 92 that is rotated to bridge between the different ports and is shown bridging between ports A and B to allow flow between those two ports. Sample exit director 90 port C is closed to prevent flow through line 86 from the second sample director 44. In one embodiment the sample exit director 90 is rotatable to allow its tube loop to align with different lines in order to change direction of flow.

Exit line 93 is connected to port A of the first sample director 42 for directing gas/liquid through MFC valve 94. A pump 98 (e.g., a vacuum pump) is connected to MFC valve 91 via gas lines 95 and 96 for removing gas/liquid from or drawing gas through the analysis system 10.

Exit line 100 is connected to port A of the second sample director 44 for directing Gas/liquid through MFC valve 102. Gas/liquid can then be removed from system 10 by pump 98 via gas line 96.

When the system is configured as shown in FIG. 1, stack gas is directed from stack gas source 16 through line 14 to the sample cell 15 of the spectrometry system 12 and is vented through line 20 out of the system 10. The spectrometry system determines the spectral analysis of the gas. Generally, this direct spectrometric analysis is used to measure components that are too high in concentration to be handled by GC or otherwise not readily amenable for chromatography or simply are in high enough concentrations to be directly analyzed by the spectrometry system 100.

On the other hand, the first input director 52, the second input director 58, the first sample loop unit 40, second sample loop unit 44, and the sample exit director 90 are configured to function in a dry mode for both of the first sample loop unit 40 and second sample loop unit 41. In more detail, the carrier gas is directed throughout the system 10. Arrows in the figure indicates gas/liquid flow which depends on the orientation of first sample director 42, second sample director 44, first input director 52, second input director 58 and sample exit director 90. Here, the carrier gas flows through the thermal desorption tubes 72, 78 under the flow control of the mass flow controllers 94, 102 and the pump 98. Thus, the system is being prepared for sample concentration.

The following configurations disclosed FIGS. 2-11 can be conducted in any order or repeated regularly or as desired.

Figure 2:
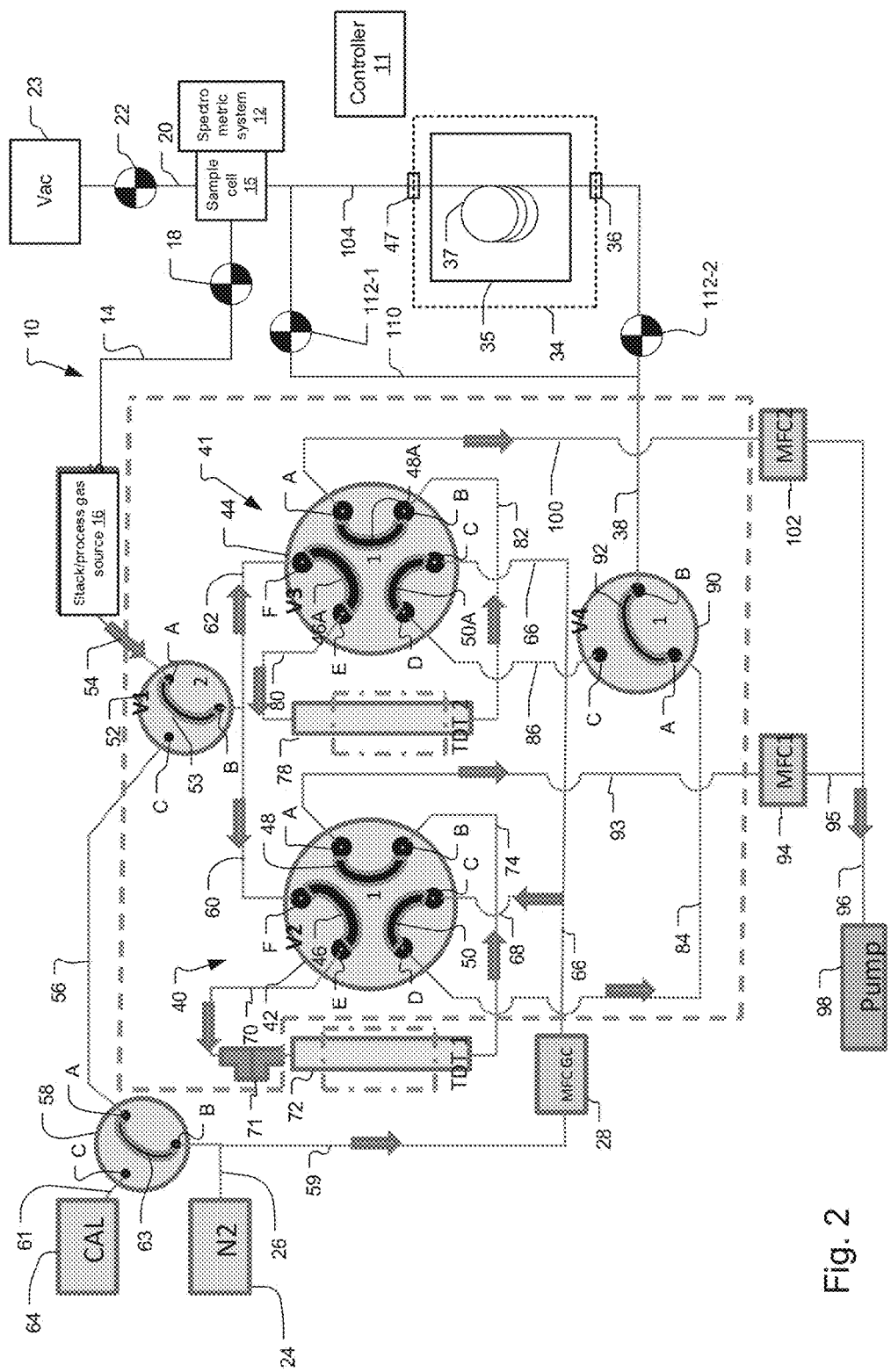
FIG. 2 is a schematic diagram of the sample analysis system showing simultaneous sampling of hazardous air pollutants or other gas samples, for example.

For measuring hazardous air pollutants (HAP) or other measurement in which the samples must first be concentrated, controller 11 configures the system as illustrated in FIG. 2. The configuration is the same as in FIG. 1 except first input director 52 is rotated so that stack gas is directed from stack gas source 16 through line 54 and port A into tube loop 53 of the first input director 52 and out through port B to the first sample loop unit 40 and the second sample loop unit 41. The first sample director 42 and the second sample director 44 direct the gas samples to their respective thermal desorption tubes 72, 78 for concentration. The flow through the thermal desorption tubes 72, 78 is controlled by the mass flow controllers 94, 102. and the pump 98 that draws the entraining air or other light gases away from the tubes while allowing certain, usually heavier, components to become trapped (e.g., by cooling to condense) within the tubes.

Additionally, at the same time, gas samples are also directed from stack gas source 16 through line 14 to the sample cell 15 of the spectrometry system 12. Depending on the desired mode of operation, sample is integrated in the cell 15, which functions as an integrating gas cell, or is directly vented through line 20 out of the system 10, in which case the gas cell 15 functions as a flow cell. Spectrometry system 12 conducts an analysis of the stack gas in the cell 15 for pollutants under the control of the controller 11, which logs and reports the results.

As a result, the configuration of FIG. 2 provides for the simultaneous sampling by: 1) analyzing the sample gas in the spectrometry system 12; and 2) the concentration of a sample in the thermal desorption tubes 72, 78.

In another mode of operation, valve 18 is closed and valve 112-1 is opened and valve 112-2 is closed allowing carrier gas to flow through the sample cell 15. This configuration allows the sample cell 15 to be flushed and also for the spectrometry system 12 to obtain background spectra.

In still another mode of operation, valve 18 is closed and valve 112-1 is closed and valve 112-2 is opened allowing carrier gas to flow through GC 35 and the sample cell 15. This configuration allows the GC and the sample cell 15 to be flushed and also for the spectrometry system 12 to obtain background spectra, which are supplied to the controller 11.

Figure 3:
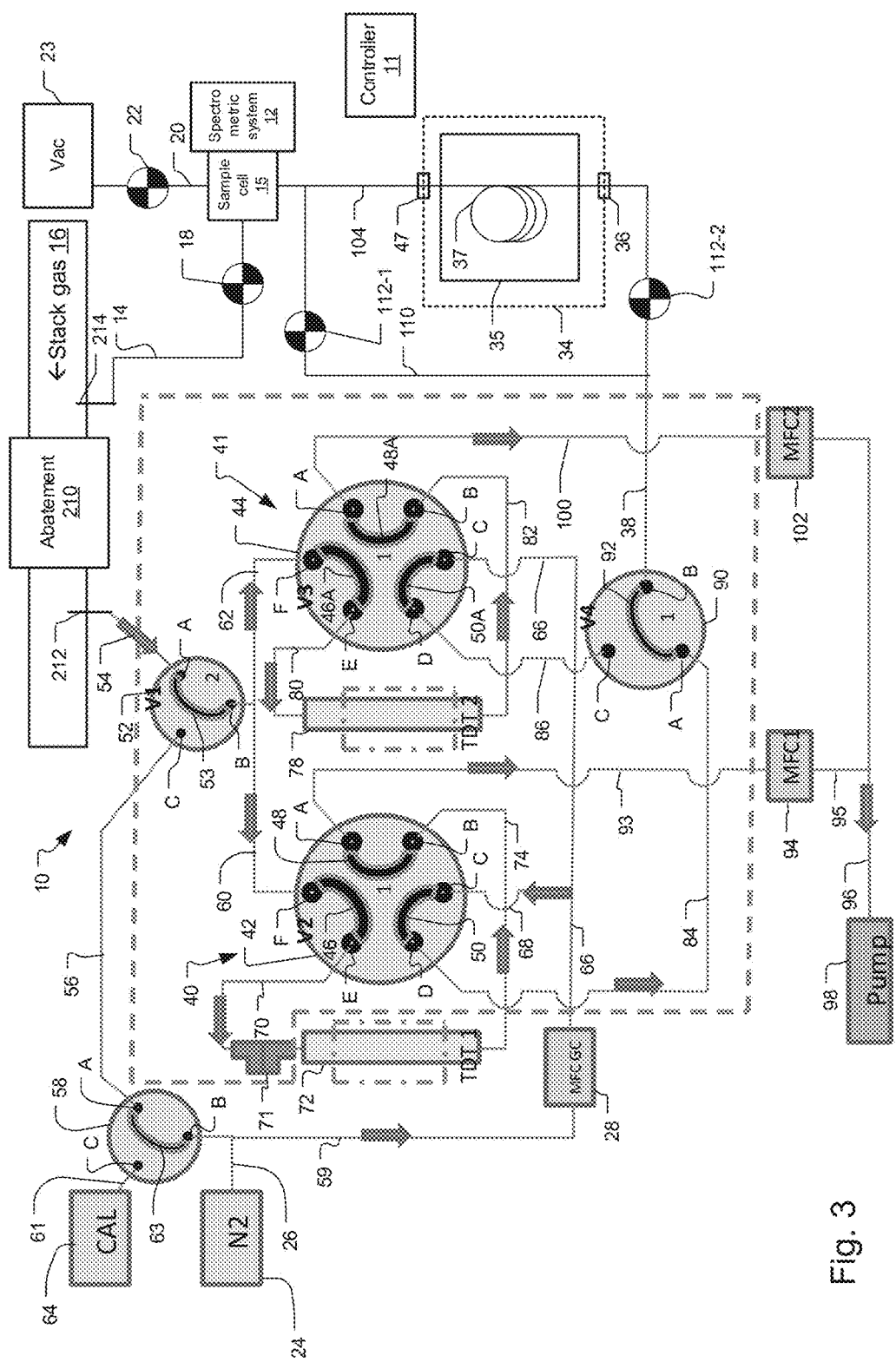
FIG. 3 is a schematic diagram of the sample analysis system for sampling and measuring hazardous air pollutants upstream and downstream of an abatement system.

FIG. 3 shows a valiant configuration that is used to test the efficacy of an abatement system 210, such as a scrubber on a stack 16 passing flue or process gasses, for example.

In more detail, an upstream probe 214 and a downstream probe 212 are inserted into the stack 16 to sample gases carried by the stack upstream and downstream of an abatement system 210. This sampling configuration allows for the analysis system 10 to measure the efficacy of the abatement system 210 and specifically assess the degree to which the abatement system 10 has removed particular components in the gasses exhausted through the stack 16.

The gases sampled by the upstream probe 214 pass through an optional filter box to remove any particulate matter or gases that need not be analyzed. These gases are drawn through the filter box and line 14, which is heated in some embodiments, by an upstream sample pump. Finally, the gases are accumulated in or pass through a sample cell 15 of the spectrometric system 12.

For the upstream gases, the concentrations of the gas components of interest are typically rather high. Thus, the spectrometric system 12 can be used in this direct sampling mode.

On the other hand, the concentrations downstream of the abatement system 210 are much lower. In order to measure these reduced concentrations, downstream samples are simultaneously captured in the desorption tubes 72 and 78 for later analysis.

Figure 6:
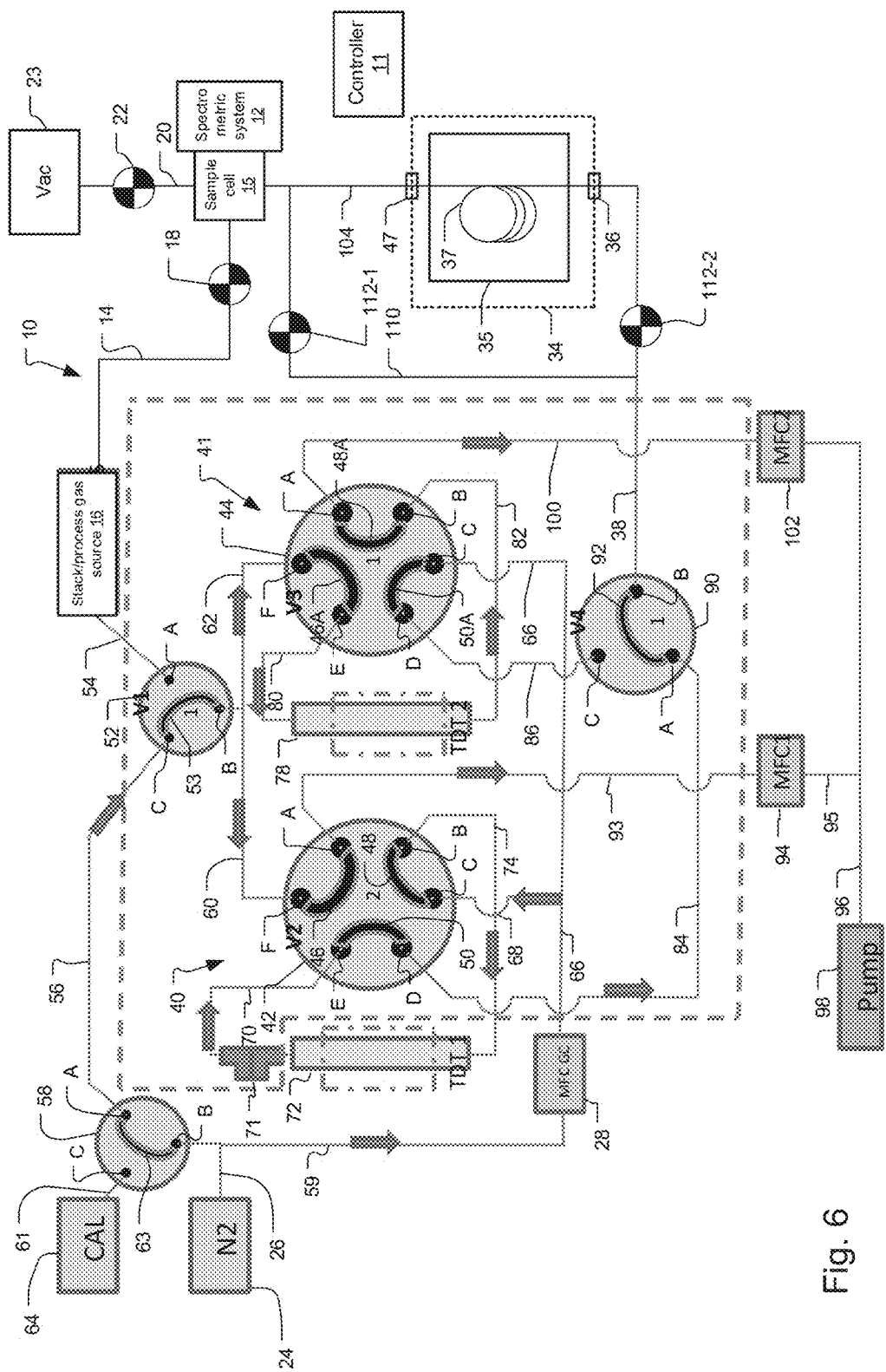
FIG. 6 is a schematic diagram of the sample analysis system where the first sampling loop is in a desorption mode and the second sampling loop is in an idle mode.
Figure 7:
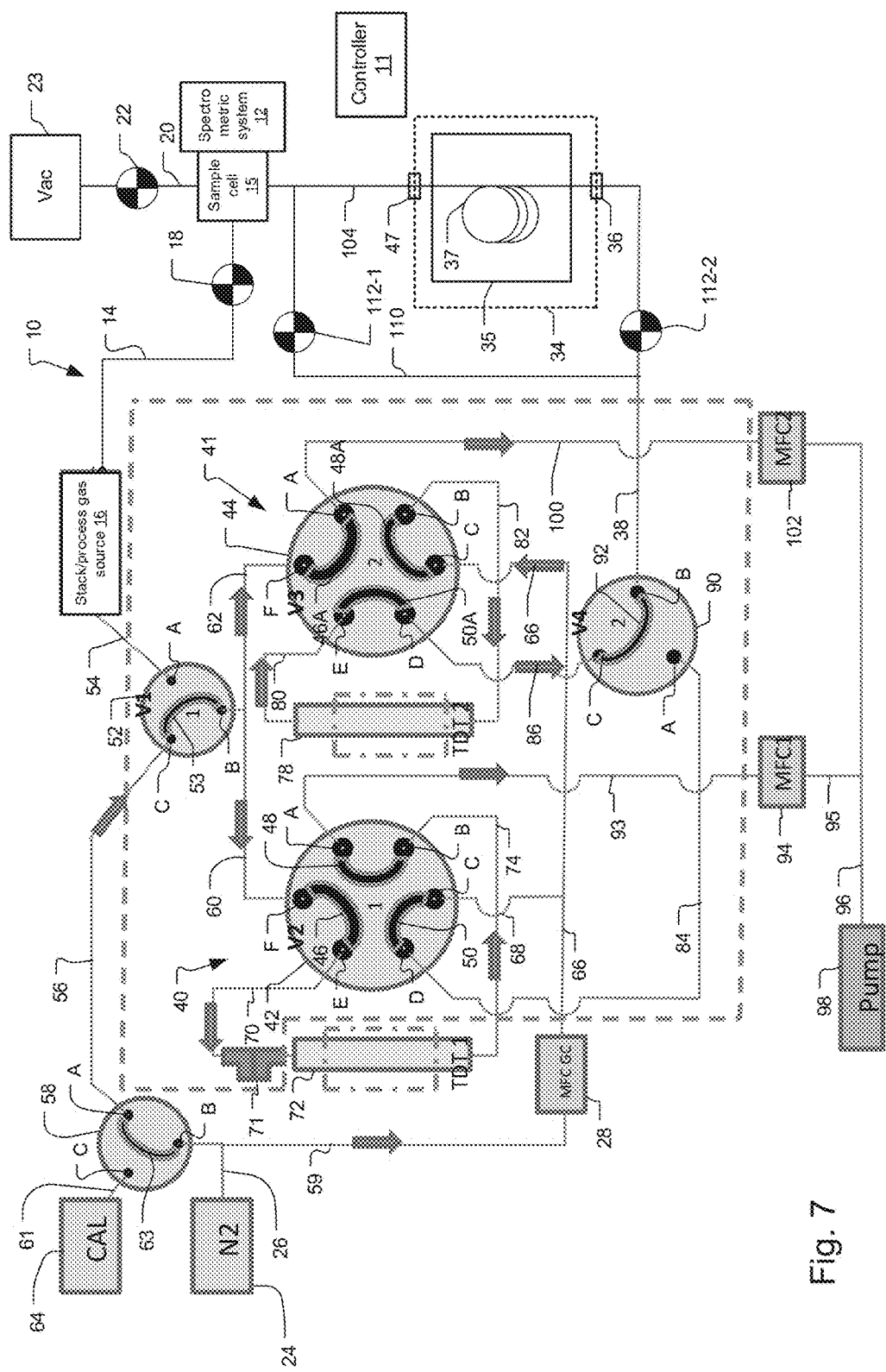
FIG. 7 is a schematic diagram of the sample analysis system where the first sampling loop is in an idle mode and the second sampling loop is in a desorption mode.

In this way, the system provides for the simultaneous sampling by: 1) analyzing the sample gas directly in the spectrometry system 12; and 2) the concentration of a sample in the thermal desorption tubes 72, 78. Then, once direct analysis is concluded, each of the desorption tubes 72, 78 can be desorbed and the concentrated samples analyzed. Specifically, in turn, configurations shown in FIG. 6 and FIG. 7 are used to analyze the samples captured in the tubes.

Figure 4:
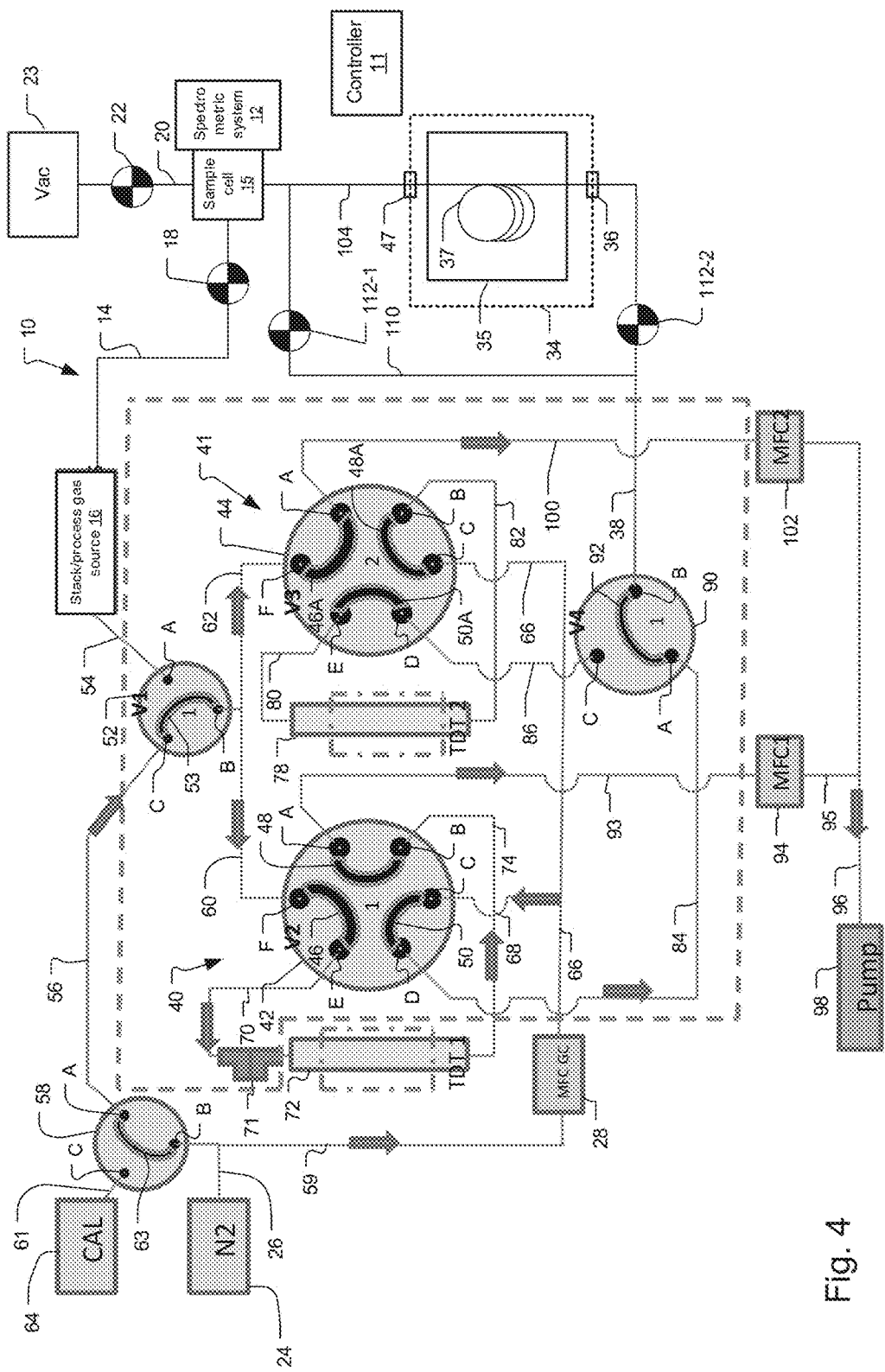
FIG. 4 is a schematic diagram of the sample analysis system where first sample loop is in dry mode, and the second sample loop is in idle mode.

A schematic configuration is displayed in FIG. 4 in which the controller 11 has configured the first sample loop unit 40 in a dry mode configuration and the second sample loop unit 41 in an idle mode configuration. Dry is to be understood as carrier gas passing through the three tube loops in a sample director and the concentrator 72. Idle is to be understood as carrier gas passing through only one tube loop in a sample director with the TUT being closed off to gas flow circulation by the sample exit director.

Carrier gas is directed from carrier gas source 24, which keeps gas circulating throughout most of the system 10. Carrier gas is directed through line 26 and line 59 to MFC valve 28. From there, a portion of the carrier gas is directed through line 66 to line 68, and enters the first sample director at port C through loop 50 to port D, and exits into line 84 to sample exit director 90 at port A. Gas passes through tube loop 92 to port B of exit director 90 and exits into line 38 to proximate end or inlet 36 of GC system 34. The carrier gas continues through the GC column 37 and exits distal end or outlet 47 through line 104 to sample cell 15 of the spectrometry system 12. Carrier gas exits the spectrometry system 12, and is vented through exit line 20 and valve 22.

A portion of the carrier gas from source 24 is also directed to port B of the second input director 58. The gas passes through tube loop 63 to port A and into line 56. Through line 56, gas is directed to port C of the first input director 52 and to port B via tube loop 53. From there, gas is directed to both line 60 and line 62. Through line 60, the gas is directed to first sample director 42 at port F through first tube loop 46 to port E and exits into line 70. From line 70, the gas passes through TDT-1 72 exits to line 74 and returns to first sample director 42 at port B, passes through second tube loop 48 to port A and into line 93. Gas flow is controlled by MFC valve 94 and exits to line 95, facilitated by pump 98, if required.

At the same time that a portion of the carrier gas exiting port B of the first input director 52 is directed through first sample director 42, another portion of the gas is directed through line 62 to second sample director 44 at port F through first tube loop 46A to port A and exits into line 100. Gas flow is controlled by MFC valve 102 and exits to line 96. From line 95 and line 96, gas is removed through pump 98 and exits analysis system 10.

Stack gas is directed from stack gas source 16 through line 14 to spectrometric system 12 and is vented through line 20 out of the system 10 in the same manner as the carrier gas from exit director 90 and in combination thereof.

Figure 5:
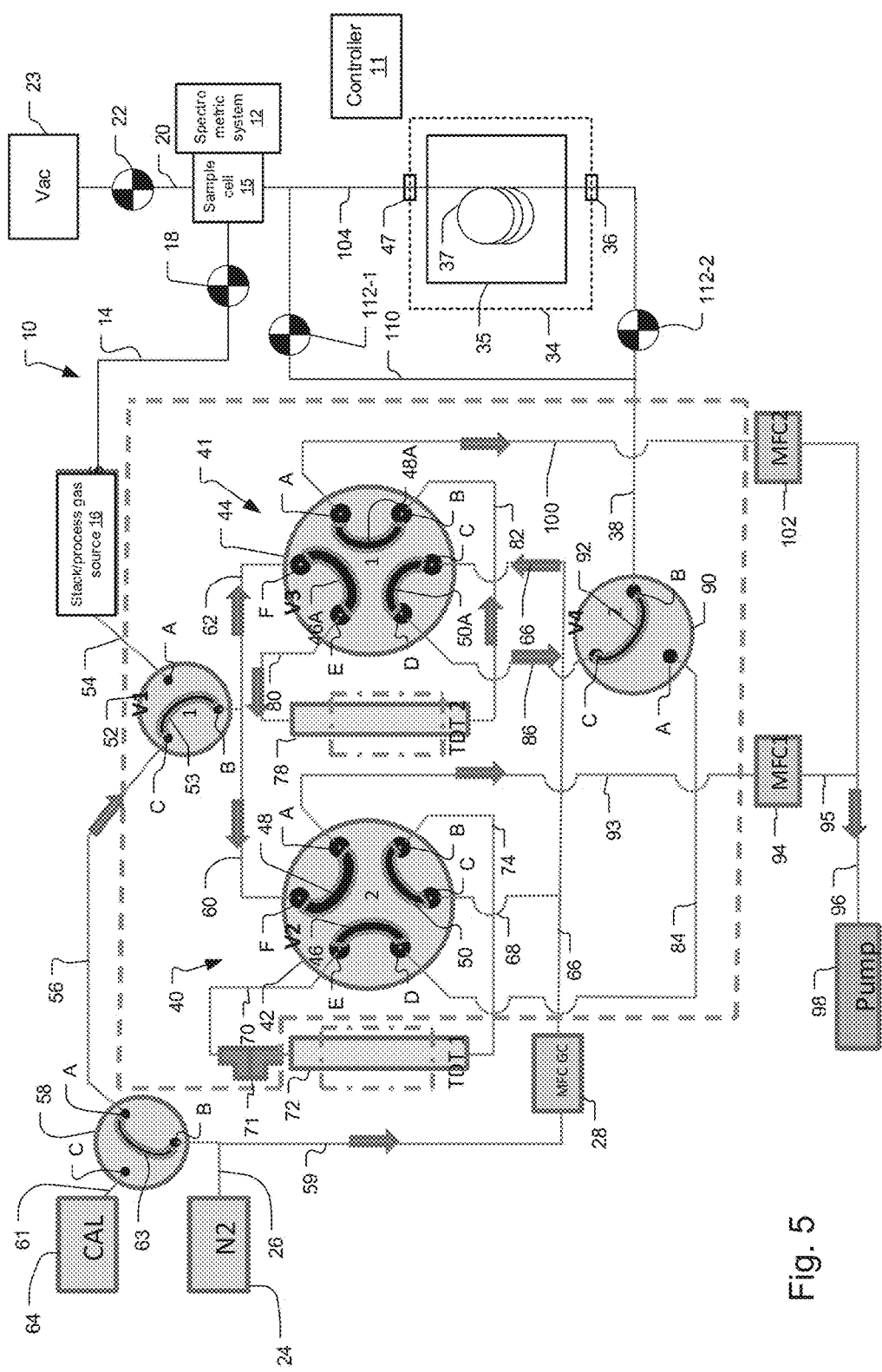
FIG. 5 is a schematic diagram of the sample analysis system where the first sampling loop is in an idle mode and the second sampling loop is in a dry mode.

A schematic configuration is displayed in FIG. 5 in which the controller 11 has configured the first sample loop 40 in an idle mode configuration and the second sample loop 41 in a dry mode configuration. The configuration is the same as in FIG. 4 except first sample director 42 is rotated one position counterclockwise so that carrier gas is directed from line 60 and port F through second first tube loop 48 to port A to line 93. TDT-1 is closed off to flow by rotating sample exit director 90 so that line 84 is closed at port A.

The second sample director 44 is configured so that gas in line 62 flows though port F and loop 46A to port E. This allows flow of carrier gas from line 62 through the director to TDT-2 78. The carrier gas is then directed via loop 48A to port A of the second sample director 44 and removed from system 10 by pump 10.

A schematic configuration is displayed in FIG. 6 in which the controller 11 has configured the first sample loop unit 40 in a desorption mode configuration and the second sampling loop 41 in a dry mode configuration.

In operation, this desorption mode for the first sample loop 40 is typically utilized after the system 10 has been configured as illustrated in FIG. 2 or FIG. 3, i.e., after a stack gas has passed through the first and second loop units 40, 41, and certain gas components have been concentrated or trapped in the desorption tubes TDT-1 and/or TDT-2. This allows the high sensitively analysis of the sample concentrated in the first thermal desorption tube TDT-1 72, for example.

Here, the first sample director 42 is rotated one position clockwise, relative to the FIG. 1 configuration, so that carrier gas is directed from line 59 to port C through tube loop 48 to port B to line 74. Thus, as the TDT-1 is heated and desorbed, carrier gas is directed to flow through TDT-1 in a direction opposite to that used for concentrating a sample component. The flow rate of carrier gas is modulated by the MFC 28 and the heating operation of the TDT 72 is controlled by the controller 11 based on the required sensitivity and the characteristics of the sample.

Sample exit director 90 set up by rotating sample exit director 90 so that line 84 is coupled to line 38 via port A and tube loop 92 and port B by the sample exit director 90.

As a result, sample gas from TDT-1 72 passes from line 70 to port E to third tube loop 50 to port D into line 84. The gas is directed through the lines to GC system 34 where the components are separated in time. These components are then analyzed in the spectrometry system 12 where the gas can be analyzed. Once a predetermined threshold is reached, the desorption loop can be stopped.

A schematic configuration is displayed in FIG. 7 in which the controller 11 as configured the second sampling loop 41 in a desorption mode configuration.

In operation, this desorption mode for the second sample loop 41 is typically utilized after the system 10 has been configured as illustrated in FIGS. 2 and 3 and possible after the sample from the first TDT-1 72 has been analyzed as illustrated in FIG. 6. This allows the high sensitivity analysis of the second sample concentrated in the second thermal desorption tube 78.

In this configuration, the second sample director 44 is rotated so that carrier gas is directed from line 59 to port C through first tube loop 48A to port AB to line 82. This allows the carrier gas to entrain the sample from TDT-2 as it is desorbed by a reverse flow through TDT-2 (in a direction opposite to that used for concentrating a sample component with a flow rate controlled by the controller 11 via control of the UFC 28. Sample exit director 90 is configured to couple line 86 (with entrained sample from TDT-2) to line 38 via port C, loop 92 and port B of the sample exit director 90, while being closed off to flow on line 84 from the first sample director 42.

As the carrier gas is directed to port C of the second sample director 44 (via line 59, MEC valve 28 and line 66), it is directed through second tube loop 48A to port B to line 82. From line 82, the carrier gas is directed in the opposite direction through second thermal desorption tube 78 to port E via line 80. After passing through the third tube loop 50A to port D into line 86, the gas is directed through the sample exit director 90 to line 38 to the GC 34 for separation. The separated components are then passed to spectrometry system 12 where the gas can be analyzed for its components. Once a predetermined threshold is reached, the desorption loop can be stopped.

Figure 8:
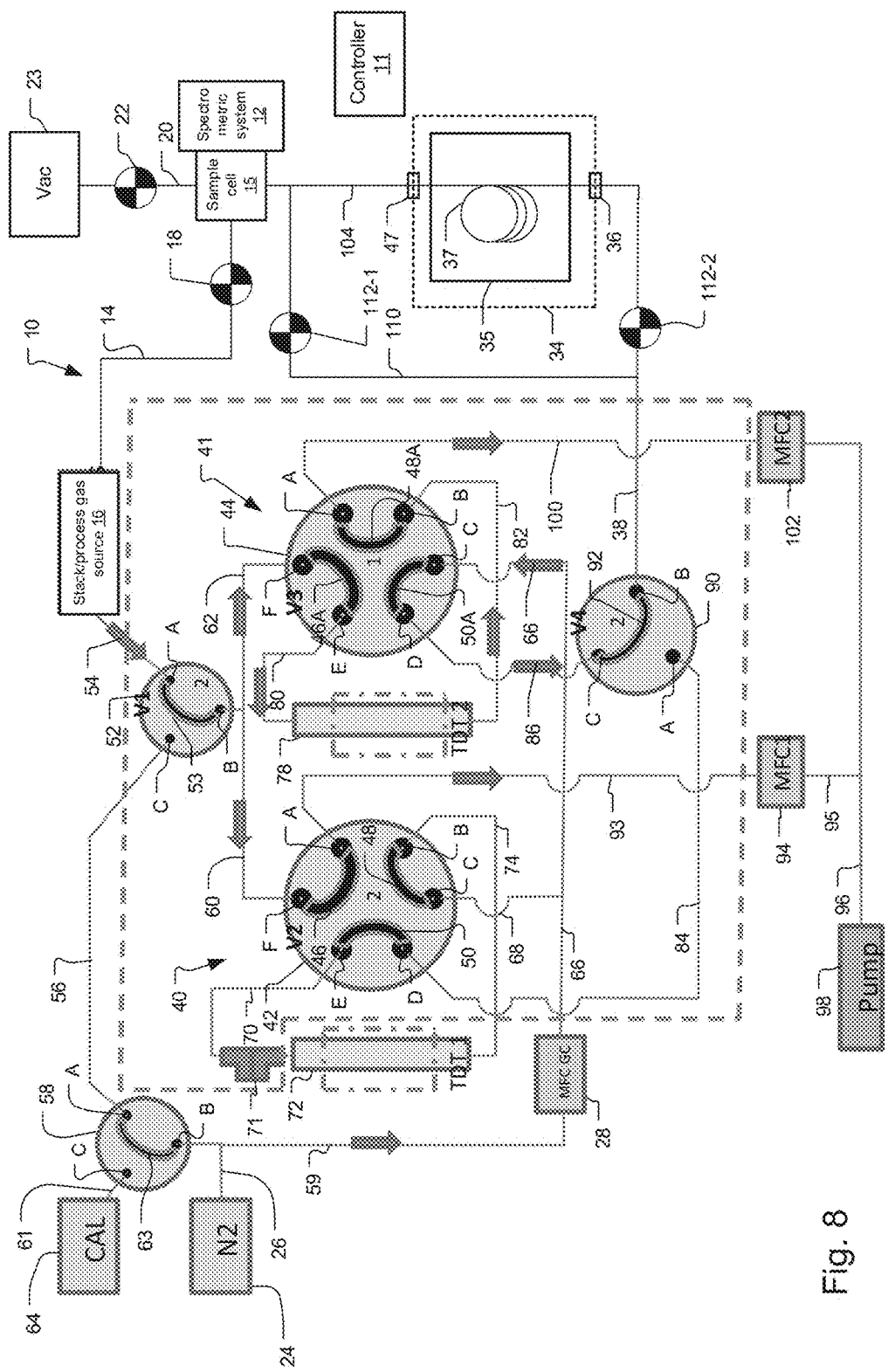
FIG. 8 is a schematic diagram of the sample analysis system where the first sampling loop is in an idle mode and the second sampling loop is in a sampling mode.

Another configuration is displayed in FIG. 8 having a first sample loop unit 40 in idle mode configuration and the second sampling loop 41 in sampling mode configuration. The first input director 52 is rotated so that stack gas can be directed from stack gas source 16 through line 54 into first sample director 52 at port A to tube loop 53 and then port B.

The first sample director 42 is rotated one position clockwise so that stack gas is directed to line 60 and to port F through first tube loop 46 to port A to line 93. From there the gas exits the system 10 at pump 98. Furthermore, TDT-1 is closed off to flow by sample exit director 90 at point C by rotating sample exit director 90 so that the tube loop 92 is not aligned with point A.

A portion of stack gas is directed from port of the first sample director 52 to line 62 where the gas is then directed to second sample director 44 at port F through first tube loop 46A to port E and exits into line 80. From line 80, the gas passes through TDT-2 78, exits to line 82 and returns to second sample director 44 at port B through second tube loop 48A to port A and into line 100. Gas flow is controlled b MIT valve 102 and exits to line 96 and pump 98. As previously explained in connection with FIG. 2, this configuration allows a sample to be captured in the second thermal desorption tube 78 at a rate modulated by the MEC 102.

In some cases, a second portion of stack or process gas is also directed from stack gas source 16 through line 14 to spectrometry system 12 for analysis. It can be either directly vented through line 20 out of the system 10 or integrated (or collected) in the sample cell 15, which is typically initialized to an evacuated state.

As a result, spectrometry system 12 conducts an analysis of the stack gas for pollutants, while the sample is also being concentrated in the second thermal desorption tube TDT-2 78. This allows for the detection of compounds in the source gas from 0.1 parts per million (ppm) to percent levels by the analysis of the spectrometry system. At a later time, with the second thermal desorption tube heated and the system is configured as shown in FIG. 7, detection in the parts per billion (ppb) or parts per trillion (ppt) levels can be performed using the combination of the GC 34 followed by the spectrometry system 12.

Figure 9:
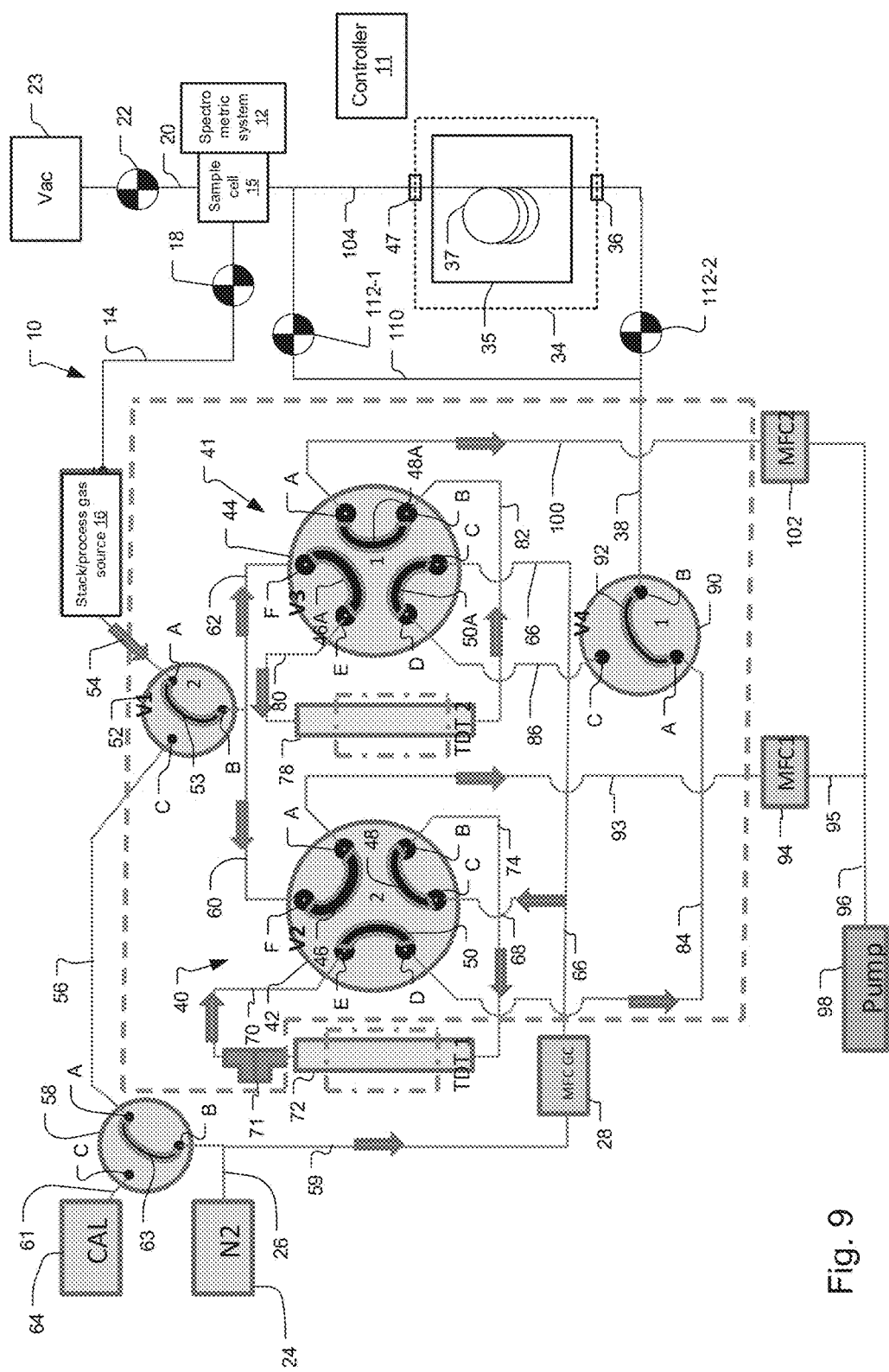
FIG. 9 is a schematic diagram of the sample analysis system where the first sampling loop is in desorption mode and the second sampling loop is in a sampling mode.

A schematic configuration is displayed in FIG. 9 having a first sample loop unit 40 in desorption mode configuration and the second sampling loop 41 in sampling mode configuration. The first input director 52 is rotated so that stack gas can be directed from stack gas source 16 through line 54 into first sample director 52 at point A to tube loop 53 and then point B.

To allow desorption, first sample director 42 is rotated one position clockwise so that a portion of stack gas is directed from line 60 to port F through first tube loop 46 to port A to line 93 and exit system 10 at pump 98. Concurrently TDT-1 is desorbed by a reverse flow of carrier gas through first sample loop unit 40. Carrier gas from gas source 24 is directed through line 59. MFC valve 28, line 66 and line 68 to port C on first sample director 42. From port C, carrier gas is directed through second tube loop 48 to port B to line 74, and through first thermal desorption tube TDT-1 72 (in a direction opposite to that used for concentrating a sample) to line 70. The gas, now entrained with one or more samples desorbed from TDT-1, is directed to port E of the first sample director 42, and passes through third tube loop 50 to port D into line 84. The gas is directed by output director 90 to gas chromatography system 34 for separation, and then spectrometry system 12 where the gas can be analyzed for desorbed. samples. Once a predetermined threshold is reached of removed contaminants, the desorption loop can be stopped.

At the same time, the second sample loop unit 41 is configured to collect and concentrate a sample in the second thermal desorption tube 78.

Figure 10:
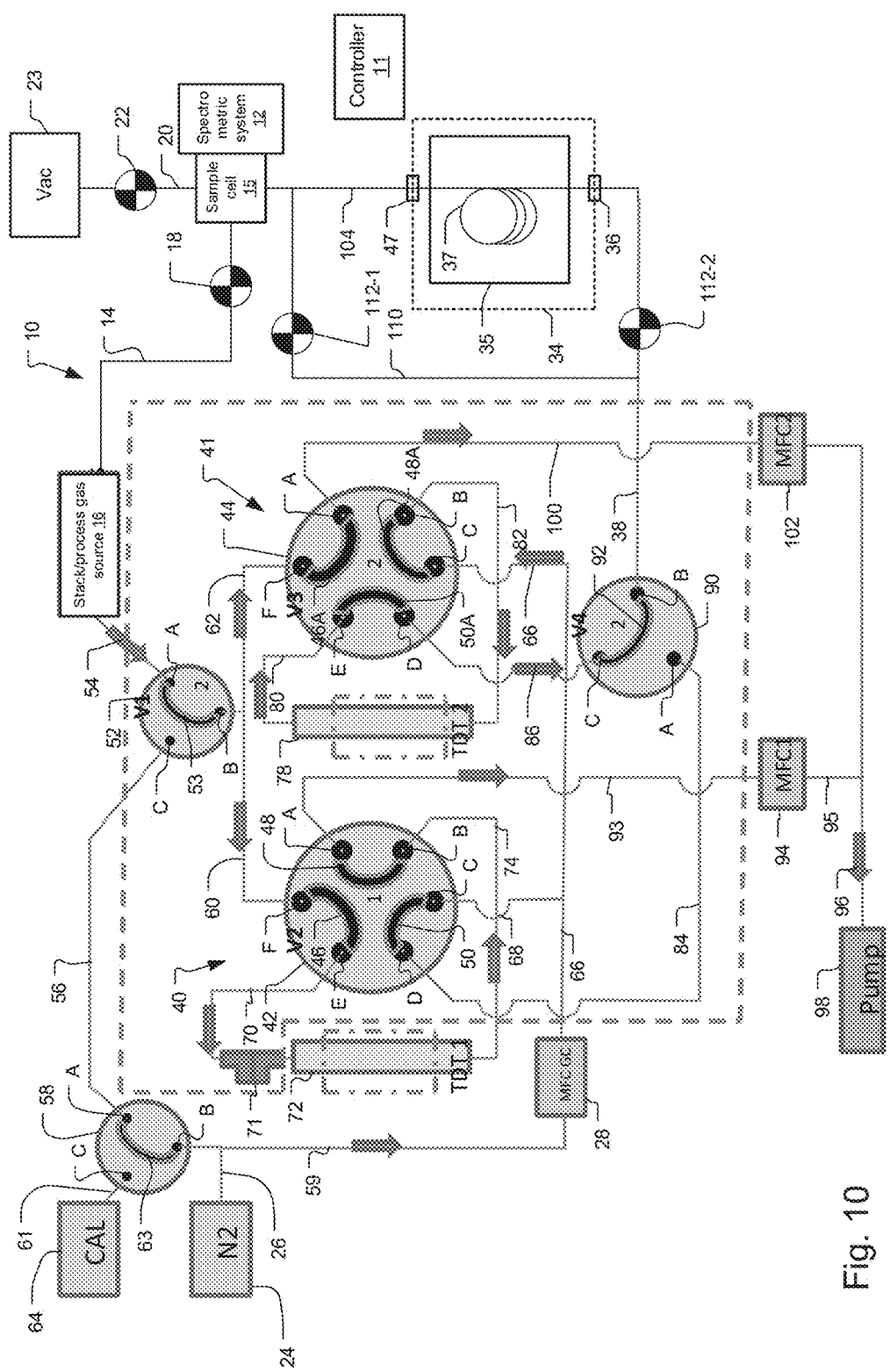
FIG. 10 is a schematic diagram of the sample analysis system where the first sampling loop is in a sampling mode and the second sampling loop is in a desorption mode.

A schematic configuration is displayed in FIG. 10 that is the reverse of the configuration shown in FIG. 9 where a first sample loop unit 40 is in sampling mode configuration and the second sample loop unit 41 in desorption mode configuration.

To allow desorption, second sample director 44 is rotated one position clockwise relative to that shown in FIG. 9. TDT-2 is desorbed by a reverse flow of carrier gas through second sample loop unit 41. Carrier gas from gas source 24 is directed through line 59, MFC valve 28 and line 66 to Port C on second sample director 44. From port C, carrier gas is directed through second tube loop 48A to port B to line 82, and directed through second thermal desorption tube TDT-2 78 (in a direction opposite to that used for concentrating a sample) to line 80. The gas, now entrained with one or more samples desorbed from TDT-2, is directed to port E on second sample director 44, and passes through third tube loop 50A to port D into line 86. The gas then enters sample exit director 90 at port C, passes through tube loop 92 to port B, and directed via line 38 to gas chromatography system 34 for separation, and then spectrometry system 12 where the gas can be analyzed for separated components. Once a predetermined threshold is reached of removed contaminants, the desorption loop can be stopped.

At the same time, with the first sample loop 40 in a sampling mode, a portion of the stack gas is directed to first sample director 42 at port F via gas line 60. The gas passes through first tube loop 46 to port E and exits into line 70. From line 70, the gas passes through TUT-1 72 for concentration and any gas that is not trapped exits to line 74 and returns to first sample director 42 at port through second tube loop 48 to port A and into line 93. Gas flow is controlled b MFC valve 94 and exits to line 95.

FIGS. 9 and 10 together illustrate how the two loops can be operated in a "ping-pong" fashion, in which one loop is capturing and concentrating a sample while the previously concentrated sample in the other loop is being analyzed.

Figure 11:
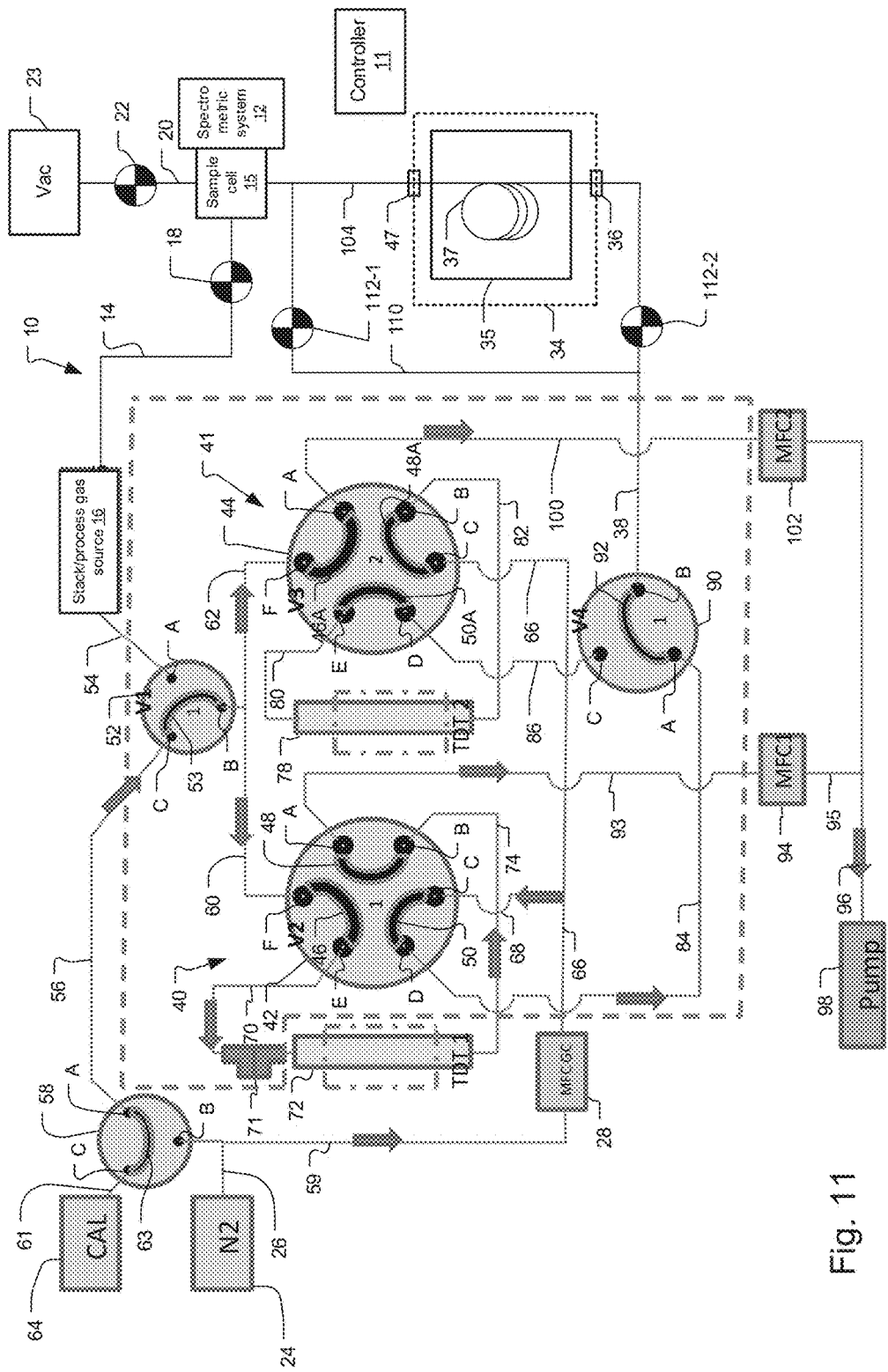
FIG. 11 is a schematic diagram of the sample analysis system where the first sampling loop is in calibrating strike sample mode and the second sampling loop is in an idle mode.

A schematic configuration is displayed in FIG. 11 having a first sample loop unit 40 in calibration spike mode configuration and the second sampling loop 41 in idle mode configuration. Here, a spiked sample (calibration gas sample) is compared to the stack gas sample (unspiked sample) to determine the compound recovery of each. This comparison helps determine whether there is any bias in the collection of the samples. For instance if the sample source has an amount of 100 nanograms (ng) and the spiking amount is 150 ng, the reading for the spiked sample should be an amount of 250 ng. Unspiked and spiked samples are alternated into spectrometry system 12. The average fraction recovered of each spiked sample needs to be between 70 and 130% for a valid test. Environmental Protection Agency regulations including Method 18—Measurement of Gaseous Organic Compound Emissions by Gas Chromatography require that two samples are collected.

In this configuration, second input director 58 is rotated as compared to its position displayed in FIG. 1. Calibration gas is directed from calibration gas source 60 through line 61 to port C, through tube loop 63 to port A and into line 56. At the first input director 52, the spiked gas is directed through first sample loop unit 40 and captured in the first thermal desorption tube 72.

Once the spike sample has been collected, the controller 11 converts the system to the configuration shown in connection with FIG. 9, for example, in which the spiked sample concentrated in the first thermal desorption tube 72 is desorbed, separated in the GC 34 and analyzed in the spectrometry system 12.

While this invention has been particularly shown and described with references to preferred embodiments thereof, it will be understood by those skilled in the art that various changes in form and details may be made therein without departing from the scope of the invention encompassed by the appended claims.

What is claimed is:

1. An analysis system configurable between a first analysis mode and a second analysis mode, the analysis system comprising:
   a spectrometric system for performing spectral analysis;
   a first sample loop unit and a second sample loop unit;
      wherein the first and second sample loop units are configured for collecting and providing samples concurrently and independently, and
   a separator for separating the samples from the first sample loop and the second sample loop into components for analysis in the spectrometric system;
   wherein, for the first analysis mode, the analysis system is configured for directing samples to the spectrometric system for spectral analysis, without passing the sample through the separator, and
   for the second analysis mode, the analysis system is configured for directing samples to the separator prior to directing the samples to the spectrometric system for spectral analysis.

2. The analysis system of claim 1, further comprising a first and a second sample concentrator in the first sample loop and the second sample loop.

3. The analysis system of claim 2, wherein each of the first and second sample concentrators is one of: a thermal desorption tube and a cryogenic trap.

4. The analysis system of claim 1, wherein the separator is a gas chromatography system.

5. The analysis system of claim 1, wherein the spectrometric system is a Fourier transform infrared system.

* * * * *